United States Patent
Cerofolini

(10) Patent No.: US 7,559,897 B2
(45) Date of Patent: Jul. 14, 2009

(54) ELECTRONIC ARRAY PROBE FOR ULTRASONIC IMAGING

(75) Inventor: Marino Cerofolini, Subbiano (IT)

(73) Assignee: Esaote, S.p.a., Casale Monferrato (IT)

( * ) Notice: Subject to any disclaimer, the term of this patent is extended or adjusted under 35 U.S.C. 154(b) by 284 days.

(21) Appl. No.: 10/883,383

(22) Filed: Jul. 1, 2004

(65) Prior Publication Data

US 2005/0033182 A1 Feb. 10, 2005

(30) Foreign Application Priority Data

Jul. 1, 2003 (EP) ................................. 03425435

(51) Int. Cl.
*A61B 8/14* (2006.01)

(52) U.S. Cl. ........................ 600/459; 600/437; 310/367; 310/369

(58) Field of Classification Search ................. 600/437, 600/439, 447, 459; 367/103, 138; 310/369, 310/367; 73/618
See application file for complete search history.

(56) References Cited

U.S. PATENT DOCUMENTS

| | | | | |
|---|---|---|---|---|
| 4,523,471 A | * | 6/1985 | Lee | 73/626 |
| 4,537,074 A | * | 8/1985 | Dietz | 73/625 |
| 4,841,977 A | * | 6/1989 | Griffith et al. | 600/439 |
| 5,563,346 A | * | 10/1996 | Bartelt et al. | 73/626 |
| 5,601,083 A | * | 2/1997 | Anderson | 600/443 |
| 5,893,832 A | * | 4/1999 | Song | 600/443 |
| 5,911,692 A | * | 6/1999 | Hussain et al. | 600/447 |
| 6,543,272 B1 | | 4/2003 | Vitek | |
| 6,582,369 B1 | * | 6/2003 | Huang et al. | 600/447 |
| 6,676,602 B1 | * | 1/2004 | Barnes et al. | 600/443 |
| 6,736,779 B1 | * | 5/2004 | Sano et al. | 600/447 |
| 6,783,497 B2 | * | 8/2004 | Grenon et al. | 600/459 |
| 2002/0068869 A1 | * | 6/2002 | Brisken et al. | 600/439 |
| 2002/0139193 A1 | | 10/2002 | Angelsen et al. | |
| 2004/0030227 A1 | * | 2/2004 | Littrup et al. | 600/300 |
| 2004/0189499 A1 | * | 9/2004 | Han et al. | 341/143 |

OTHER PUBLICATIONS

Fjield, T. et al., "The combined concentric-ring and sector-vortex phased array for MRI guided ultrasound surgery", *IEEE Transactions on Ultrasonics, Ferroelectrics and Frequency Control*, Sep. 1997, IEEE, USA, vol. 44, No. 5, pp. 1157-1167.

* cited by examiner

*Primary Examiner*—Long V Le
*Assistant Examiner*—Ellsworth Weatherby
(74) *Attorney, Agent, or Firm*—Woodard, Emhardt, Moriarty, McNett & Henry LLP

(57) ABSTRACT

An electronic array probe for ultrasonic imaging includes an array of transmitting and/or receiving electroacoustic transducers arranged in concentric bands in which the transducers are tangent to one other in both radial and circumferential directions. In order to minimize the number of transducers required without compromising dynamic range, a transducer arrangement geometry is provided so that the number of transducers having the same focusing delay is minimal or null.

21 Claims, 4 Drawing Sheets

$A_i$ with $i \in \{2, 4, 6, 8, 10, 12, .., n \text{ even}\}$
Annular bands with position of even order number $A_i$ with $i \in \{1, 3, 5, 7, 11, .., n \text{ odd}\}$
Annular bands with position of odd order number

ELECTRONIC ARRAY PROBE FOR ULTRASONIC IMAGING

CROSS-REFERENCE TO RELATED APPLICATION

The present application claims the benefit of European Patent Application Serial No. 03425435.9 filed on Jul. 1, 2003, which is hereby incorporated by reference in its entirety.

BACKGROUND

This invention relates to electronic array probes for ultrasonic imaging, and in particular, to electronic array probes that comprise an array of transmitting and/or receiving electroacoustic transducers.

In the operation of electronic array probes, an ultrasonic beam is swept over a region of interest by electronic means which electronically generates time delays for acoustic radiation from each transducer. Thanks to this technique, the ultrasonic beam, which is generated by the acoustic contributions from all transducers, may be focused on one point, line or area of the region of interest, or the beam may be steered.

However, conventional two-dimensional array probes have the drawback of requiring a relatively large number of transducers in order to obtain sufficient resolution, resulting in the cable that connects the transducers to the controller having a large number of conductors, i.e., at least one conductor per transducer. This is a serious limitation, particularly for endocavitary or intraluminal probes, which are designed to be introduced in orifices or canals of the human or animal body, and are subjected to well-defined strict size restrictions. Therefore, both cable selection and probe installation are problematic and expensive, and also cause the probe to be more delicate to meet size restrictions that are barely compatible with the ideal size for endocavitary or intraluminal examinations.

Two different arrangements are known in the art to obviate this drawback. A first known arrangement provides for the use of a multiplexer and a cable having as many conductors as are needed for a subset of the total number of transducers, such that conductors are alternately switched to different subsets of transducers by the multiplexer. In addition to cost problems, the multiplexer is still a space-requiring electronic device, so therefore the problem is only partly solved. Also, while the multiplexing process allows the use of cables having a reduced number of conductors, i.e. smaller cables, it requires longer scanning times, as the whole transducer array is excited by way of a transducer subset exciting sequence, causing a longer beam forming time in addition to focusing or steering delays.

An alternative arrangement is known as a sparse array probe. Sparse arrays are two-dimensional arrays in which not all transducers are connected to the controller or not all the transducers are present. Hence, the number of conductors in the cable for connecting the probe to the control apparatus is actually reduced, but the acoustic signal dynamic range, i.e. the major to minor lobe ratio, is also reduced. Secondary or minor lobes are related to the number of transducers in the array. Therefore, sparse array probes typically have a large number of transducers, making them unsuitable for use in endocavitary probes.

A few examples of the foregoing arrangements are further detailed in U.S. Pat. Nos. 5,537,367 and 6,419,633.

U.S. Pat. No. 4,797,682 describes an endocavitary probe in which transducers are arranged in annular concentric bands and are adjacent and tangent to one another both within their respective annular bands and between annular bands, and in which transducers have identical extensions or active radiating areas in any one of the annular bands, and different extensions of active radiating areas from one band to the other. Transducers are described to have such sizes that the spacing between transducers, i.e. between the centers of the radiating surfaces of transducers, is irregular and does not account for the current restriction that requires spacing not to exceed half the wavelength of the acoustic pulse. While transducer arrays according to U.S. Pat. No. 4,797,682 provide encouraging results, they still have the drawback of requiring a large number of transducers having different sizes, whereby attention has to be paid during design to ensure that size differences actually work to minimize the number of transducers that, in the worst-case scan plane condition, have identical focusing delays on that plane. Therefore, the design of these types of probes is difficult and their construction requires a considerable number of transducer types having different radiating areas. More generally, there is no rule that allows for a reduction in the number of different transducers by providing a way to determine the number, pattern and type of the transducers required to form a predetermined array while obtaining the desired results.

Also, in the arrangement according to the above mentioned patent, transducer sizes vary from one annular band to the other; hence, the overall power delivered by each transducer varies according to its radiating area.

In the prior art, there are no phased array endocavitary probes that provide good dynamic range, i.e. sufficient major to minor lobe ratio, good resolution, and relatively low cost that allow them to be used with low-priced ultrasonic imaging apparatus.

From the technical point of view, the solution to this problem requires two contrasting requirements to be fulfilled. In fact, the attainment of high resolution and dynamic range, i.e. an optimized major to minor or side lobe ratio, requires the provision of a large number of transducers, and high dynamic range further requires spacing between transducer centers to be as small as possible, whereas probe size and cost reduction requires a reduction of the number of transducers, which affects resolution and dynamic range.

Therefore, the need arises for phased array ultrasonic probes which have a small size and a sufficient number of transducers such as to provide an optimized resolution and an optimized dynamic range, and which can be fabricated at such cost as to be able to be used with low-priced ultrasonic imaging apparatus, i.e., at very low costs.

SUMMARY OF THE INVENTION

The present invention achieves the above purposes by providing a probe as described hereinbefore in which transducers are arranged within the array with such a geometry that, given the worst-case scan plane, the number of transducers having the same focusing delay on a scan point, line or area, is minimal or null.

DETAILED DECRYPTION OF THE PREFERRED EMBODIMENTS

Figure 1:
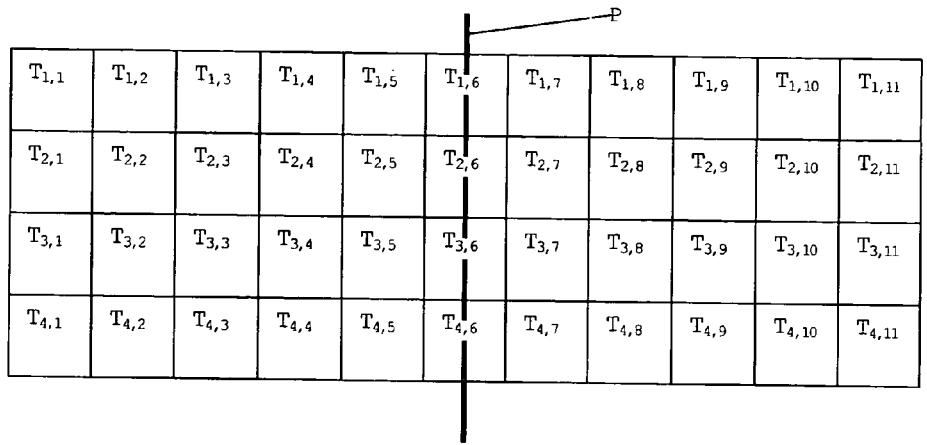
FIG. 1 shows a highly simplified example of a transducer array with reference to a scan plane on which the beam resulting from the contributions of the array transducers is to be focused.

With reference to FIG. 1, there is shown an array having a rectangular arrangement of eleven columns and four rows of transducers. Given a scan plane that is perpendicular to the array and has a direction parallel to the columns and coincident with the median axis of the sixth column, i.e., the central column, the delays imparted to the transducers of each column are substantially identical; hence all the transducers of each column have the same or almost the same effect on dynamic range as a single transducer whose size would be equal to the sum of the four transducers of each column. Hence, the effect on dynamic range is substantially the same as would be obtained with a linear array of eleven transducers having the same size as the sum of the four transducers of each column (see FIG. 2). Therefore, only eleven transducers are actually effective for dynamic range, i.e. major lobe to minor lobe, ratio purposes, and not the forty-four transducers that are present in the array. Hence, the invention is based on the discovery that the number of transducers is redundant in a phased array probe, and that it is important to find a spatial arrangement of transducers that allows the minimization, in an unfavorable scan plane condition, of the transducers that have identical focusing delays on such plane, i.e., those transducers that are of no help in improving dynamic range.

Figure 3:
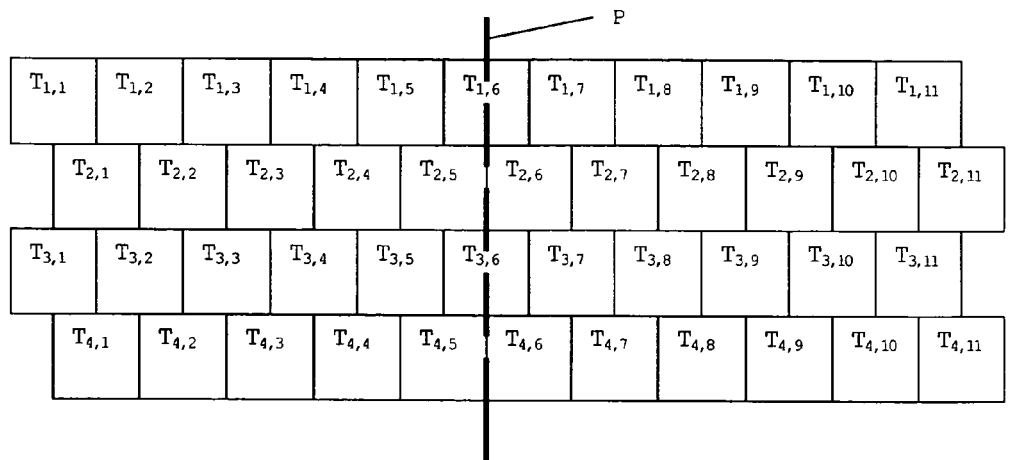
FIG. 3 is a highly simplified view of a geometrical arrangement of transducers in which the number of transducers that have the same focusing delay on the scan plane of FIG. 1 is minimized.

An arrangement provided by this invention is shown in FIG. 3 in its simplest form and with reference to the previous example of FIG. 1. An advantageous arrangement provides that each row of transducers of the four rows of the array be staggered with respect to the two rows adjacent thereto. It is apparent that, given a scan plane like the one of FIG. 1, the arrangement of FIG. 3 has no transducers of aligned columns that might be equaled to a single larger transducer, for dynamic range purposes. In this arrangement each line of transducers is staggered by half the transducer width; hence the interfaces between the individual transducers of each row are in a central position with respect to the interfaces between the transducers of the rows adjacent thereto.

The arrangement of FIG. 3 provides dynamic range advantages when considering the worst-case scan plane with respect to the transducer arrangement of FIG. 1. If such a scan plane is changed with reference to the transducer arrangement of FIG. 3, the worst-case scan plane then is substantially the one oriented parallel to the centers of staggered transducer with respect to the arrangement of FIG. 1. Therefore the number of transducers needed in a worst-case case condition sufficient to provide an acceptable dynamic range, i.e., there are a sufficient number of redundant transducers having equal delays, nevertheless results in a reduction in the number of transducers required in the array. Obviously, in a better scan plane, the number of transducers having different delays that cannot be integrated or interpreted as a single transducer increases and, as a result, dynamic range is improved as compared with the worst-case case situation.

The arrangement of transducers may be further improved by providing an annular, circular or elliptical pattern of transducers in which each row of transducers is arranged in an annular band concentric to the others with the radial interfaces between transducers being disposed in staggered positions with respect to the interfaces of the transducers on adjacent bands. Particularly, the radial interfaces between the transducers of a row may be provided in an intermediate position with respect to the circumferential extension of the transducers of the adjacent annular bands, or they may be radially aligned with the centers of the transducers of the adjacent annular bands.

In accordance with a preferred arrangement, the same number of transducers is provided in each concentric annular band. Here, advantages may be obtained by compensating for the increase of the angular extension, proportional to the increase of the radius of the annular band, by reducing the radial width of the band in such a manner that all the transducers have the same radiating size within predetermined tolerances. From the geometrical point of view, this involves an increase of the angular width of transducers and a reduction of the radial extension of the transducers as annular bands become larger. Obviously, the central portion of the array is a full circular element, and the transducers are not provided as annular segments, but as circular segments of such central portion.

According to a preferred exemplary embodiment, each annular band is divided into sixteen parts having the same area. In this embodiment, 12 annular bands are provided, including the central circular element, whereas 16 transducers are provided for each annular band and for the central circular element. Therefore, the resulting transducer array has 192 transducers which are provided in such a geometric arrangement and in such a size that, given the worst-case plane, in terms of number of transducers having the same radiating focusing delay, there are always at least 64 transducers in the array that have different focusing delays. This number of transducers is sufficient to maintain both resolution and dynamic range, i.e. major to side or minor lobe ratio, at a high level.

In order to further widen the aperture of the probe, the invention further provides that the transducer array is not disposed over a plane but over a surface shaped as a spherical or elliptical sector. In the case of a transducer arrangement over a circular surface divided into adjacent annular bands and a central circular element, a spherical surface is suitably provided whose center coincides with the center of the annular bands. In the case of a transducer arrangement over an elliptical surface, divided into elliptical annular bands with a central elliptical element, as described above regarding the circular arrangement, the ellipsoid segment is disposed with the two foci coincident with the plane that contains the two foci of the elliptical bands and the central elliptical element. This permits a widening of the aperture of the transducer array.

A variant of the previously described embodiment provides a different transducer staggering pattern across the annular bands, with respect to their radial position and to the radial positions of transducers on adjacent bands. Here, instead of providing a constant staggering pattern equal to half the angular width of the transducers of a band with respect to the transducers of the adjacent bands, given n annular bands of transducers, including the central disk-shaped area, the radial interfaces between transducers are radially aligned with the centers of the transducers of the inwardly adjacent band, or in an intermediate position between the radial interfaces of the transducers of the inwardly adjacent band only for annular bands designated with even numbers, with the central disk-shaped area being designated with number 1. For annular bands designated with odd numbers, starting from band 3, the interfaces of the odd-numbered annular bands are situated in an intermediate position between the ideal extension of the interface between two adjacent transducers of the central element and the radial extension of the radial interface between the transducers of the annular band that is radially inwardly adjacent to the odd annular band, which radial extension of the interface between two transducers of the annular radially inwardly adjacent band is angularly closer to the ideal extension of the radial interface between two transducers of the central element.

This transducer arrangement rule causes an increase in the number of transducers having different focusing delays, given a radial scan plane coincident with a radial interface between two adjacent transducers of the central area, thereby increasing the number of transducers having different focusing delays to be greater than 64.

Obviously, the two examples described are not the only possible examples and any transducer staggering arrangement may be provided, recursive rules being preferred, as they obviously facilitate assembly operations.

The advantages of the present invention are self-evident from the above description. The staggered arrangement of transducers for each annular band and the selection of annular circular, elliptical or oval bands allows the minimization or elimination of transducers having equal acoustic beam focusing delays in the worst-case-case scan plane. By this arrangement the number of effective dynamic range improving transducers is always high for any scan plane. Furthermore, this is obtained while considerably reducing the overall number of transducers in the transducer array, thereby minimizing the number of conductors in the cable that connects the array to the control means of the ultrasonic imaging apparatus. It shall be noted that the above concept not only applies to ultrasonic beam transmission, but also to ultrasonic beam reception. An optimal compromise is thus obtained between the total number of transducers in the array and the minimum number of transducers having different delays with reference to the worst-case scan plane. This results in a compromise between the requirement for high resolution and dynamic range and the requirement for a smaller size probe having a smaller number of conductors connecting the transducers to the ultrasonic imaging apparatus.

By way of further detail, FIG. 1 schematically shows an array of electroacoustic transducers T1,1 to T4,4. Therefore, the array of electroacoustic transducers Ti,j has 44 transducers arranged in 11 columns and 4 rows. P designates a scan plane perpendicular to the surface of the transducer array and to the rows, whereas the column 6 is cut into two halves.

Considering the scan plane P and the geometric arrangement of transducers Ti,j in the array of FIG. 1, the ultrasonic beam obtained from the transducers may be only focused on a line of the scan plane, that is, if the transducers of each column have the same focusing delays. In that condition, the contributions of the transducers of each column to dynamic range, i.e. to major to side or minor lobe ratio, is equal to the contribution of a single transducer for each column, i.e. a transducer whose radiating area corresponds to the sum of the radiating areas of the transducers Ti,j of a column.

Figure 2:
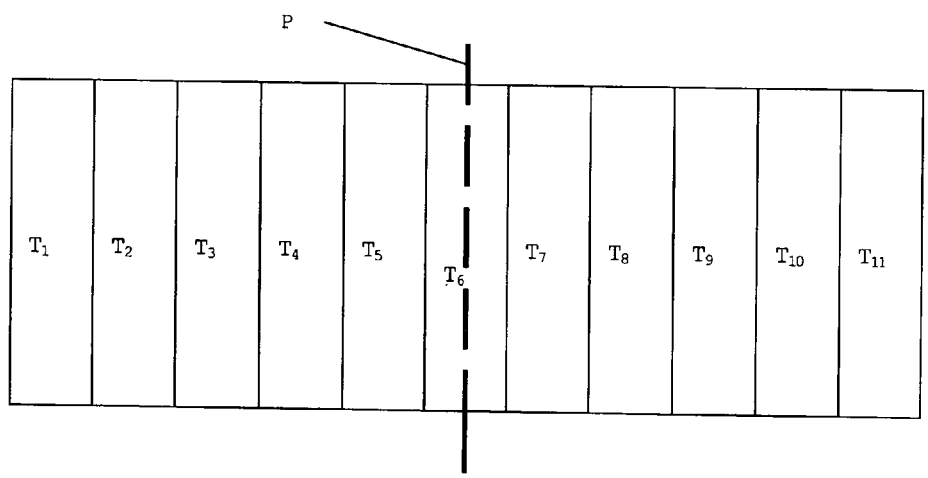
FIG. 2 shows how, with reference to the scan plane of FIG. 1, the transducers of the array of FIG. 1 have identical delays.

This equivalence is shown in FIG. 2. Therefore, in these conditions, the number of transducers in the array is drastically reduced and, since dynamic range depends both on transducer spacing, i.e. the distance between the centers of the radiating surfaces thereof, and on the number of the transducers in the array, dynamic range is obviously degraded for the acoustic pulse focused on the plane P. An obvious and natural manner to obviate this problem is to increase the number of transducers so that, in the worst-case scan plane conditions, the number of transducers excited with different focusing delays provides sufficient dynamic range.

FIG. 1 clearly shows that, in order to obtain, for instance, 64 transducers with different delays, an array with 64 columns of transducers is to be provided, and no advantage is provided by increasing the number of transducers within each column, i.e., by increasing the number of rows. Nevertheless, by increasing the number of transducers the array size is also increased, as well as the number of connecting wires between each transducer and the controller electronics, i.e., the beamformer. This increase in size, and especially in the number of the connecting wires, is dramatically in contrast with the need to maintain small sizes of ultrasonic endocavitary probes.

The present invention is meant to act on transducer arrangement geometries and to minimize or eliminate transducers having equal focusing delays for a worst-case scan plane. Both the orientation of the worst-case scan plane and the possibility of minimizing or eliminating transducers having identical focusing delays depends on the basic selection of the transducer arrangement geometry in the array. A rectangular array is certainly not the most advantageous arrangement pattern, but it was selected to illustrate more accurately and simply the concept on which this invention is based. FIG. 3 shows a transducer array as modified according to the inventive teaching. Here, the simplest arrangement is shown, in which the rows of transducers are staggered by half the extension of the transducers in the longitudinal direction of rows. Both even rows are staggered in the same direction with respect to odd rows. The scan plane P is the same as in FIGS. 1 and 2. This simple geometrical pattern clearly shows that transducers excited with different focusing delays on the plane P number twice as many as those of FIG. 1.

Figure 4:
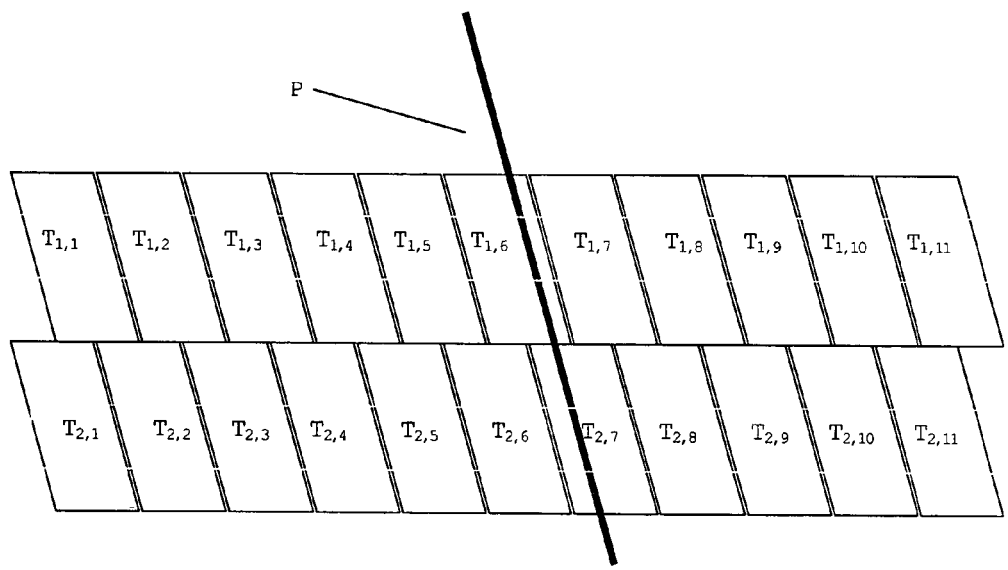
FIG. 4 shows, with reference to a scan plane defined to be inclined along the lines that join the centers of the transducers of staggered rows, the transducers having different delays on an unfavorable scan plane.

FIG. 4 shows a different scan plane P which is oriented perpendicular to the array surface, but parallel to the lines that join the centers of the transducers of two adjacent odd and even rows. Once more, with reference to this plane, transducers having different focusing delays number twice as many as in the condition of FIG. 2. The transducer arrangement geometry of FIG. 3 is equivalent, with reference to the plane P of FIG. 4, to two staggered rows of transducers, each of which is composed of transducers whose size equals the size of the transducers of rows 1 and 2 and 3 and 4, respectively, of the same column as is shown in FIG. 3.

This rectangular arrangement geometry is not optimal, as it does not match the geometry of the anatomic parts which are typically examined using endocavitary probes having a tubular shape with a round section, and it does not allow further minimizing of the number of transducers having the same focusing delays for the worst-case scan plane.

Figure 5:
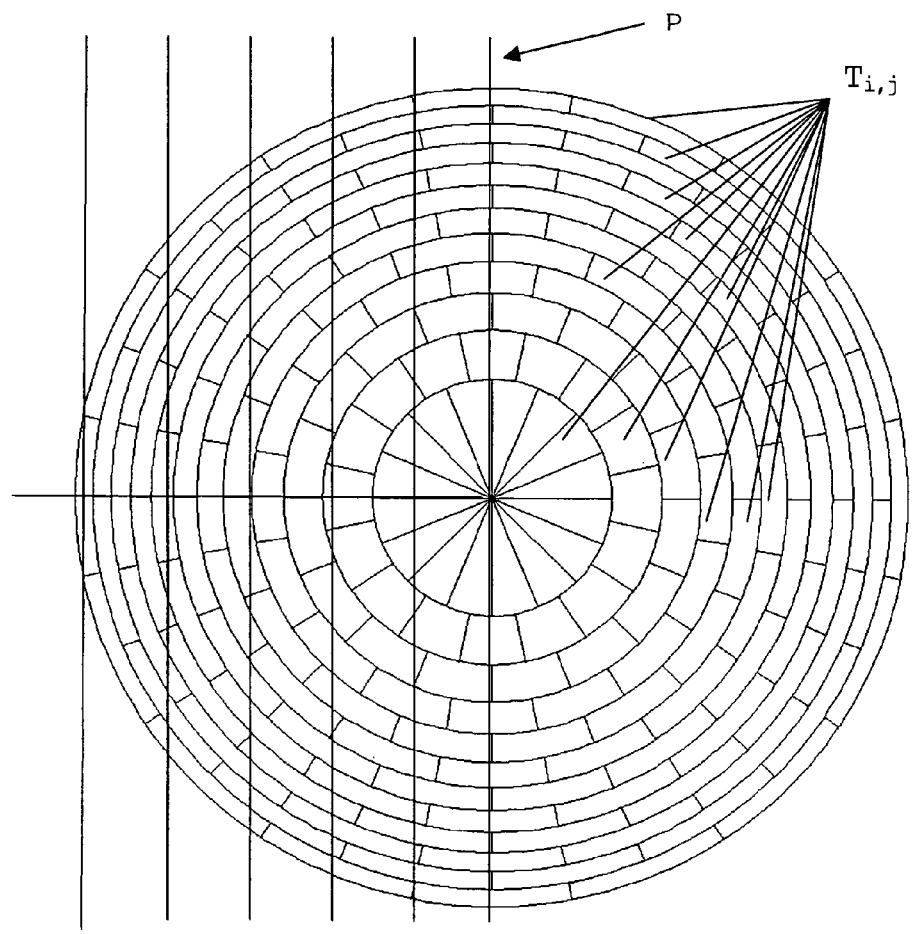
FIG. 5 is a plan view of an array according to this invention.

FIG. 5 shows a transducer arrangement pattern according to a preferred embodiment of this invention which is based on circular symmetry. Here, transducers are arranged on annular bands, except in the central area, which is formed by a disk-shaped element. The central disk and each peripheral concentric annular band are divided into equal numbers of transducers having the same area and angular extension. However, the radial interfaces of transducers between the central disk and the first annular band and between adjacent annular bands are staggered with respect to each other by half the angular extension of the transducers of adjacent bands, with the central disk being also counted as a band.

In such a simple arrangement, if the annular bands had the same radial width, the transducers of outward annular bands would have increasing scan areas as compared with those of inward annular bands. This would require different radiating/receiving power for transducers across the different bands, and would require compensation of transducer excitation for radiating the acoustic wave and processing the received signal.

In order to avoid such additional work, which would increase the complexity of transducer control and controller electronics, and would cause probes of this type to be only used in existing apparatus in a difficult or indirect manner, or a change being required for the control of transducers having different radiating/receiving areas, all the transducers in the transducer array according to the embodiment of FIG. 5 have the same radiating size. This is obtained, according to this invention, by progressively reducing the radial width of the individual concentric bands as the radius thereof increases. A preferred embodiment of the invention is designed to include a total of 192 transducers, which have the same area and are disposed on concentric annular bands. The 192 elements are arranged on 11 concentric annular bands and a central circular element all having the same size, each of the annular bands and the central disk being divided into 16 equal-size portions, each of which corresponds to a transducer element, whereas the center of each element is situated at the radial edge of the elements of the outwardly adjacent band and of the inwardly adjacent band with the inwardly adjacent band for the first annular band being the central disk. Given an array having an outer diameter=12 mm, the total area of the array is:

$$S = \frac{\pi d^2}{4}$$

Therefore, the area of each of the 12 circular elements, i.e. the 11 bands and the central disk-shaped element, is:

$$S_1 = \frac{S}{12}$$

and the area of each of the 192 transducers is:

$$S_2 = \frac{S_1}{16}$$

Then, the radii of the annular bands and the central disk are determined by:

$$r_1 = \frac{d_1}{2} = \frac{1}{2}\sqrt{\frac{4S_1}{\pi}}$$

for the central disk and by $$r_1 = \frac{d_1}{2} = \frac{1}{2}\sqrt{\frac{S_1 + 0.7854 d_{i-1}^2}{0.7854}}$$

for annular bands.

This geometry minimizes the number of transducers having identical focusing delays in the worst-case scan plane condition, to such an extent that, even in the worst-case condition, at least 64 transducers having different focusing delays on the worst-case scan plane are provided. The transducer arrangement geometry also has a simple construction, as transducers may be intuitively arranged relative to position and size in a unique error-free order during fabrication. Also, while the total number of transducers is reasonably small, a relatively large number of transducers having different focusing delays is provided in the worst-case scan conditions, so that the number of transducers is sufficient to provide an optimized dynamic range.

Regarding construction, the number of differently sized and shaped transducers is reasonably small, as transducers follow a well-defined size and shape rule. Only 12 circular bands including the central disk are provided, which all have identical transducers within the same band. Transducers may be also easily increased in number by the addition of outer annular bands, so that a basic array having a minimum acceptable size may be maintained for every probe. Larger transducer arrays may be obtained starting from a minimum array, with transducers being simply added to one or more of the outer radial bands. This is particular advantageous in terms of fabrication costs.

Figure 6:
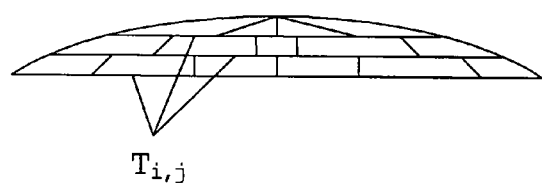
FIG. 6 is an exemplified arc shape of an array of the type as shown in FIG. 5.

Referring to FIG. 6, the aperture angle of the array may be widened, particularly in endocavitary probes, by disposing the array of FIG. 5 over a spherical or cap-shaped surface in lieu of a plane surface. FIG. 6 illustratively shows such a spherical surface divided into concentric annular spherical bands, which are in turn divided into a certain number of transducers. The number of bands and transducers shown is only intended to illustrate the inventive principle.

Figure 7:
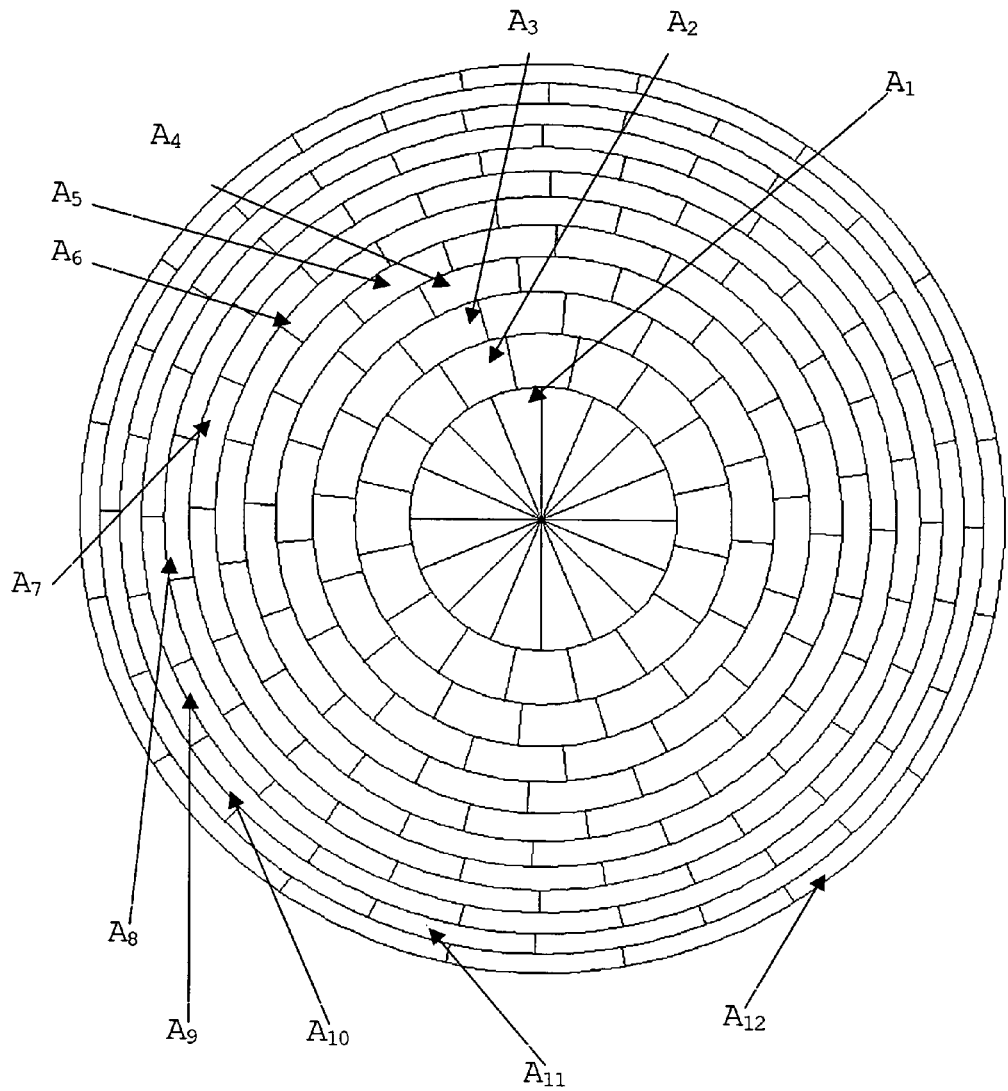
FIG. 7 is a view similar to FIG. 5, showing a variant embodiment of the circular array as shown in FIG. 5.

A variant of the previously described embodiment is shown in FIG. 7 and envisages a different transducer staggering pattern across the annular bands Ai, relative to the radial position of transducers with respect to the radial positions of the transducers of the adjacent bands Ai−1 and Ai+1, where i=0, 1, . . . , n. Here, instead of providing a constant staggering pattern equal to half the angular width of the transducers of a band Ai with respect to the transducers of the adjacent bands Ai−1 and Ai+1, given n annular bands of transducers, including the central disk-shaped area, designated as A1, the radial interfaces between transducers are radially aligned with the centers of the transducers of the inwardly adjacent band Ai, or in an intermediate position between the radial interfaces of the transducers of the inwardly adjacent band Ai only for annular bands Ai designated with even "i" numbers, with the central disk-shaped area being designated with number 1. For annular bands designated with odd numbers, starting from band 3, the interfaces of the odd-numbered annular bands are situated in an intermediate position between the ideal extension of the interface between two adjacent transducers of the central element A1 and the radial extension of the radial interface between the transducers of the annular band Ai−1 that is radially inwardly adjacent to the odd-numbered annular band, which radial extension of the interface between two transducers of the annular radially inwardly adjacent band is angularly closer to the ideal extension of the radial interface between two transducers of the central element. This transducer arrangement rule causes an increase in the number of transducers having different focusing delays, given a radial scan plane coincident with a radial interface between two adjacent transducers of the central area, which provides a number of transducers having different focusing delays greater than 64.

Obviously, the two examples described are not the only possible examples and any transducer staggering arrangement may be provided, recursive rules being preferred, as they obviously facilitate assembly operations.

While the simplest embodiment relates to a rectangular array and a preferred embodiment relates to a circular array, the invention shall not be intended to be restricted to these two shapes, but also applies to other geometrical shapes, e.g., to polygonal arrays having more than four sides, oval elliptical arrays, or arrays resulting from the combination of the above mentioned shapes, those shapes being determined, for example, by the field of use of the transducer array or the probe which includes it.

What is claimed is:

1. An electronic array probe for ultrasonic imaging, comprising an array of electroacoustic transducers, said transducers being arranged in adjacent positions on concentric annular bands, said transducers being tangent to one another in both radial and circumferential directions, characterized in that said transducers are arranged within said array with such a geometry that the number of transducers having the same focusing delay with respect to a scan point, scan line or scan area, is minimal or null, a central portion adjacent to the innermost annular band, wherein each annular band and said central portion contain identical numbers of transducers, wherein each annular band of transducers contains a predetermined number of transducers, each transducer having a geometric center, each transducer being disposed with its geometric center angularly staggered with respect to the geometric centers of the transducers of the adjacent bands, or the central portion, by a constant length from band to band, said length being a rational fraction of the angular displacement of said transducer.

2. A probe as claimed in claim 1, characterized in that said annular bands have a polygonal shape.

3. A probe as claimed in claim 1, characterized in that said annular bands have a round shape.

4. A probe as claimed in claim 1, characterized in that said annular bands have an elliptical shape.

5. A probe as claimed in claim 1, characterized in that said annular bands have a spherical shape.

6. A probe as claimed in claim 1, characterized in that said annular bands have a shape formed as a combination of one or more of polygonal, round, elliptical or spherical shapes.

7. A probe as claimed in claim 1, characterized in that said central portion is composed of a set of transducers that wholly cover the area delimited by the inner perimeter of said innermost annular band.

8. A probe as claimed in claim 1, characterized in that each of said transducers of said transducer array have the same radiating and/or receiving area, such that the radial width of the outer annular bands decreases with the increase of the radius of said radial bands and of the angular displacement of said transducers on said annular bands.

9. A probe as claimed in claim 1, characterized in that the transducers of each annular band have the shape of a sector of their respective annular band, said transducers having the same radial width as their respective annular band, whereas said transducers of the central portion have the shape of circular segments.

10. A probe as claimed in claim 1, comprising at least eleven annular bands and said central portion, each annular band comprising 16 transducers.

11. A probe as claimed in claim 1, characterized in that said annular bands have a polygonal shape, with the central portion having a corresponding polygonal shape.

12. A probe as claimed in claim 1, characterized in that said annular bands have a circular shape, with the central portion having a corresponding circular shape.

13. A probe as claimed in claim 1, characterized in that said annular bands have an elliptical shape, with the central portion having a corresponding elliptical shape.

14. A probe as claimed in claim 1, characterized in that said transducer array is disposed over a plane.

15. A probe as claimed in claim 1, characterized in that said transducer array is disposed over a surface having the shape of a spherical sector, said annular bands being concentrically disposed thereon.

16. A probe as claimed in claim 1, characterized in that said transducer array is disposed over a surface having the shape of ellipsoid, said annular bands being concentrically disposed thereon.

17. A probe as claimed in claim 1, characterized in that said transducer array is disposed over a surface having the shape of a polygon, said annular bands being concentrically disposed thereon.

18. A probe as claimed in claim 1, wherein said probe is a part of a modular set of probes having transducer arrays with different numbers of transducers, said transducer arrays being provided with a minimum predetermined number of transducers, said number of transducers of said sets of probes being increased by the addition of one or more outer annular bands of transducers.

19. A probe as claimed in claim 1, characterized in that said probe contains 192 transducers, wherein said transducers exhibit at least 64 different excitation and/or reception delays.

20. A probe as claimed in claim 1, characterized in that each transducer has a geometric center, the radial interfaces between said transducers are radially aligned with the geometric centers of said transducers of the inwardly adjacent band which defines an ideal extension between the interfaces of adjacent trandsucers, or in an intermediate position between the radial interfaces of said transducers of said inwardly adjacent band only for said annular bands designated with even numbers, said center-most band or area being designated as number 1, and that for said annular bands designated with odd numbers, starting with band number 3, said interfaces of bands are situated in an intermediate position between the ideal extension of the interface between two adjacent transducers of said central-most band or area and the radial extension of the radial interface between said transducers of said band that is radially inwardly adjacent to said odd-numbered band, said radial extension of said interface between said two transducers of said radially inwardly adjacent band being angularly closer to said ideal extension of said radial interface between said two transducers of said center-most band or area.

21. An electronic array probe for ultrasonic imaging, comprising an array of electroacoustic transducers, said transducers being arranged in adjacent positions on concentric annular bands, said transducers being tangent to one another in both radial and circumferential directions, characterized in that said transducers are arranged within said array with such a geometry that the number of transducers having the same focusing delay with respect to a scan point, scan line or scan area, is minimal or null, a central portion adjacent to the innermost annular band, wherein each annular band and said central portion contain identical numbers of transducers, wherein the transducers of a band are angularly staggered with respect to the transducers of the band adjacent thereto and to the transducers of said central portion, such that the centers of the transducers of said band are radially aligned with the radial edges that delimit the adjacent transducers of adjacent annular bands and of said central portion.

* * * * *